United States Patent
Baggen et al.

(10) Patent No.: US 9,176,932 B2
(45) Date of Patent: Nov. 3, 2015

(54) METHOD FOR DETECTING FALLS AND A FALL DETECTOR

(75) Inventors: Constant Paul Marie Jozef Baggen, Blerick (NL); Ningjiang Chen, Shanghai (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 468 days.

(21) Appl. No.: 13/478,403

(22) Filed: May 23, 2012

(65) Prior Publication Data

US 2013/0138395 A1 May 30, 2013

Related U.S. Application Data

(63) Continuation-in-part of application No. 13/510,408, filed as application No. PCT/IB2010/055319 on Nov. 22, 2010.

(30) Foreign Application Priority Data

Nov. 25, 2009 (CN) .......................... 2009 1 0226557

(51) Int. Cl.
*G01P 15/00* (2006.01)
*G01C 5/06* (2006.01)
*G06F 17/18* (2006.01)
*A61B 5/00* (2006.01)
*A61B 5/11* (2006.01)

(52) U.S. Cl.
CPC .............. *G06F 17/18* (2013.01); *A61B 5/1117* (2013.01); *A61B 5/7246* (2013.01); *G01C 5/06* (2013.01); *G01P 15/00* (2013.01)

(58) Field of Classification Search
CPC ..... G01P 15/00; G01P 15/001; G01P 15/003; G01P 15/005; G01C 5/06; G06F 17/18; G06F 17/00
USPC ........... 702/181, 81, 127, 138–139, 141, 150, 702/179, 182, 188–189; 703/2, 4, 17; 706/45–48; 600/587, 592, 595; 73/1.37–1.38, 1.75–1.77, 1.79, 384
See application file for complete search history.

(56) References Cited

U.S. PATENT DOCUMENTS

| 2006/0236761 A1 | 10/2006 | Inoue et al. |
| 2007/0030159 A1 | 2/2007 | Stoev et al. |
| 2007/0030587 A1 | 2/2007 | Noda et al. |

FOREIGN PATENT DOCUMENTS

| EP | 1974662 | 10/2008 |
| WO | WO2004114245 | 12/2004 |
| WO | WO2009138900 | 11/2009 |

OTHER PUBLICATIONS

Tao et al., Fall Incidents Detection for Intelligent Video Surveillance, 2005 IEEE, 5 pp.*

(Continued)

*Primary Examiner* — Toan Le

(57) ABSTRACT

A method for detecting a fall by a user includes a method of detecting a fall by a user. The method includes processing measurements obtained from one or more sensors to extract a respective value for a plurality of features associated with a fall. A respective log likelihood ratio for each of the values is determined. Whether the user has fallen is determined based on the determined log likelihood ratios.

18 Claims, 8 Drawing Sheets

(56) References Cited

OTHER PUBLICATIONS

Bianchi et al., Falls Event Detection Using Triaxial Accelerometry and Barometric Pressure Measurement, Sep. 2-6, 2009, 31st Annual International Conference of the IEEE EMBS, Minneapolis, Minnesota, pp. 6111-6114.*

A.K. Bourke et al., "The Identification of Vertical Velocity profiles Using an Inertial Sensor to Investigate Pre-impact Detection of Falls", ScienceDirect, Medical Engineering & Physics 30 (2008) 937-946.

N. Noury et al., "A Proposal for the Classification and Evaluation of Fall Detectors", ScienceDirect, 29 (2008), pp. 340-349.

Bourke et al: "Fall-Detection Through Vertical Velocity Thresholding Using a Tri-Axial Accelerometer Characterized Using an Optical Motion-Capture System"; 30th Annual International IEEE EMBS Conference, Vancouver, British Columbia, Canada, Aug. 20-24, 2008, pp. 2832-2835.

Wu: "Distinguishing Fall Activities From Normal Activities by Velocity Characteristics"; Journal of Biomechanics 33 (2000), pp. 1497-1500.

* cited by examiner

METHOD FOR DETECTING FALLS AND A FALL DETECTOR

CROSS-REFERENCE TO RELATED APPLICATIONS

This application is a Continuation-in-Part application under 35 USC §120 of U.S. application Ser. No. 13/510,408, filed May 17, 2012, the contents of which is incorporated herein by reference.

TECHNICAL FIELD OF THE INVENTION

The invention relates to a method for detecting falls by a user and a fall detector, and in particular the invention relates to a method and a fall detector that has an improved fall detection rate and a reduced false alarm rate.

BACKGROUND TO THE INVENTION

Falls affect millions of people each year and result in significant injuries, particularly among the elderly. In fact, it has been estimated that falls are one of the top three causes of death in elderly people. A fall can be defined as a sudden, uncontrolled and unintentional downward displacement of the body to the ground followed by an impact.

Personal Help Buttons (PHBs) are available that require the user to push the button to summon help in an emergency. However, if the user suffers a severe fall (for example if they are knocked unconscious), the user might be unable to push the button, which might mean that help doesn't arrive for a significant period of time, particularly if the user lives alone.

Fall detectors are also available that process the output of one or more movement sensors to determine if the user has suffered a fall. However, it has been found that these fall detectors have an unfavourable trade-off between fall detection probability and false alarm rate.

Given that a high false alarm rate will result in additional costs to the organisation responsible for giving assistance to the user of the fall detector (i.e. they will need to contact or visit the user of the fall detector when the fall detection alarm is triggered) and that a high false alarm rate is undesirable for the user of the fall detector, it has been found that an economically viable fall detector should provide a false alarm rate of, say, less than one false alarm in each two-month period, while maintaining a (positive) fall detection probability above 95 percent.

Most existing body-worn fall detectors make use of an accelerometer (usually a 3D accelerometer that measures acceleration in three dimensions) and they try to infer the occurrence of a fall by processing the time series generated by the accelerometer. Some fall detectors can also include an air pressure sensor, for example as described in WO 2004/114245. However, these existing fall detectors do not meet the detection requirements set out above.

Thus, one of the main disadvantages of existing fall detectors is their moderate reliability as expressed by a Receiver Operating Curve (ROC). The ROC expresses the achievable probability of detecting a fall versus the false alarm probability for different settings of parameters of a given system.

Even with an extended set of features (i.e. determining more than just an impact from the accelerometer measurements and a change in height from the pressure sensor measurements), it has been found that it is difficult to obtain a satisfactory performance if each feature is simply compared to a threshold and the subsequent reasoning only involves the feature-wise binary outcomes of these comparisons.

Therefore, there is a need for an improved method for detecting falls.

SUMMARY OF THE INVENTION

According to a first aspect of the invention, there is provided a method of detecting a fall by a user, the method comprising a method of detecting a fall by a user, the method comprising processing measurements obtained from one or more sensors to extract a respective value for a plurality of features associated with a fall; determining a respective log likelihood ratio for each of said values; and determining whether the user has fallen based on the determined log likelihood ratios.

According to a second aspect of the invention, there is provided a fall detector, comprising a processor that is configured to process sensor measurements to extract a respective value for a plurality of features associated with a fall, determine a respective log likelihood ratio for said values and to determine whether the user has fallen based on the determined log likelihood ratios.

According to a third aspect of the invention, there is provided a computer program product comprising computer-readable code that, when executed on a suitable computer or processor, is configured to cause the computer or processor to perform the steps in the method described above.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
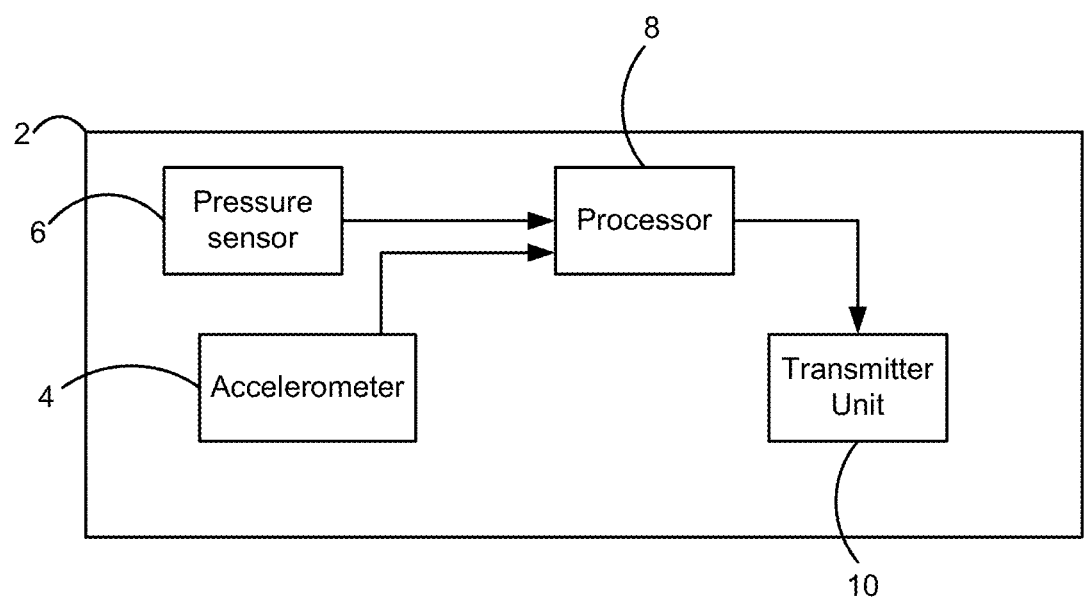
FIG. 1 is a block diagram of a fall detector in accordance with the invention.

A fall detector 2 according to an embodiment of the invention is shown in FIG. 1. The fall detector 2 is designed to be worn by a user, for example on their wrist, at their waist or on their chest or back, without adversely affecting the movement or balance of the user. In a preferred embodiment, such as that shown in FIG. 1, the fall detector 2 can be designed as a pendant to be worn around the neck of the user.

In this exemplary embodiment, the fall detector 2 comprises two sensors, an accelerometer 4 and pressure sensor 6, which are connected to a processor 8. The processor 8 receives measurements from the sensors 4, 6, and processes the measurements to determine if a user of the fall detector 2 has suffered a fall.

The fall detector 2 also comprises a transmitter unit 10 that allows the fall detector 2 to transmit an alarm signal to a base station associated with the fall detector 2 (which can then issue an alarm or summon help from a healthcare provider or the emergency services) or directly to a remote station (for example located in call centre of a healthcare provider) if a fall is detected, so that assistance can be summoned for the user.

In some embodiments (not represented by the fall detector shown in FIG. 1), the fall detector 2 can further comprise an audible alarm unit that can be activated by the processor 8 in the event that the processor 8 determines that the user has suffered a fall. The fall detector 2 may also be provided with a button that allows the user to manually activate the audible alarm unit if they require assistance (or deactivate the alarm if assistance is not required).

The operation of the processor 8 will now be described in more detail.

In order for the processor 8 to determine if the user has suffered a fall, it is necessary to extract values for various features that are associated with a fall from the sensor measurements.

For example, a fall can be broadly characterised by a change in altitude of around 0.5 to 1.5 meters (depending on the part of the body that the fall detector 2 is to be worn), culminating in a significant impact (i.e. a sharp deceleration), followed by a period in which the user does not move very much. Thus, in order to determine if a fall has taken place, the processor 8 needs to process the sensor measurements to extract values for features including a change in altitude, a maximum activity level around the time that the change in altitude occurs, an impact magnitude and a period in which the user is relatively inactive following the impact.

In one embodiment of the invention, in order to minimise the power consumption of the fall detector 2 (and hence extend the battery life of the fall detector 2) the processor 8 operates according to a "lazy evaluation" principle using a state machine. Thus, the processor 8 extracts a value for a feature from the sensor measurements and only extracts a value for a subsequent feature if the value for the previously extracted feature does not preclude a fall having taken place. Thus, as soon as the processor 8 identifies a value for a feature that precludes a fall having taken place, the processor 8 decides that the event is not a fall, and the processor 8 returns to its lowest state.

If the event is such that the processor 8 extracts values for all of the specified features, then the processor 8 can switch to a reasoning state in which the processor 8 determines if the current event (to which the extracted values of the features relate) is a fall.

In further embodiments, it may be that the processor 8 has states for separately recognizing "free falls" (i.e. for detecting when the user has dropped the fall detector 2) and when a fall alarm is revoked (for example the fall alarm could be revoked if the fall detector 2 detects that the user starts to move after a fall or the alarm could be revoked by the user if the alarm is a false alarm).

Figure 2:
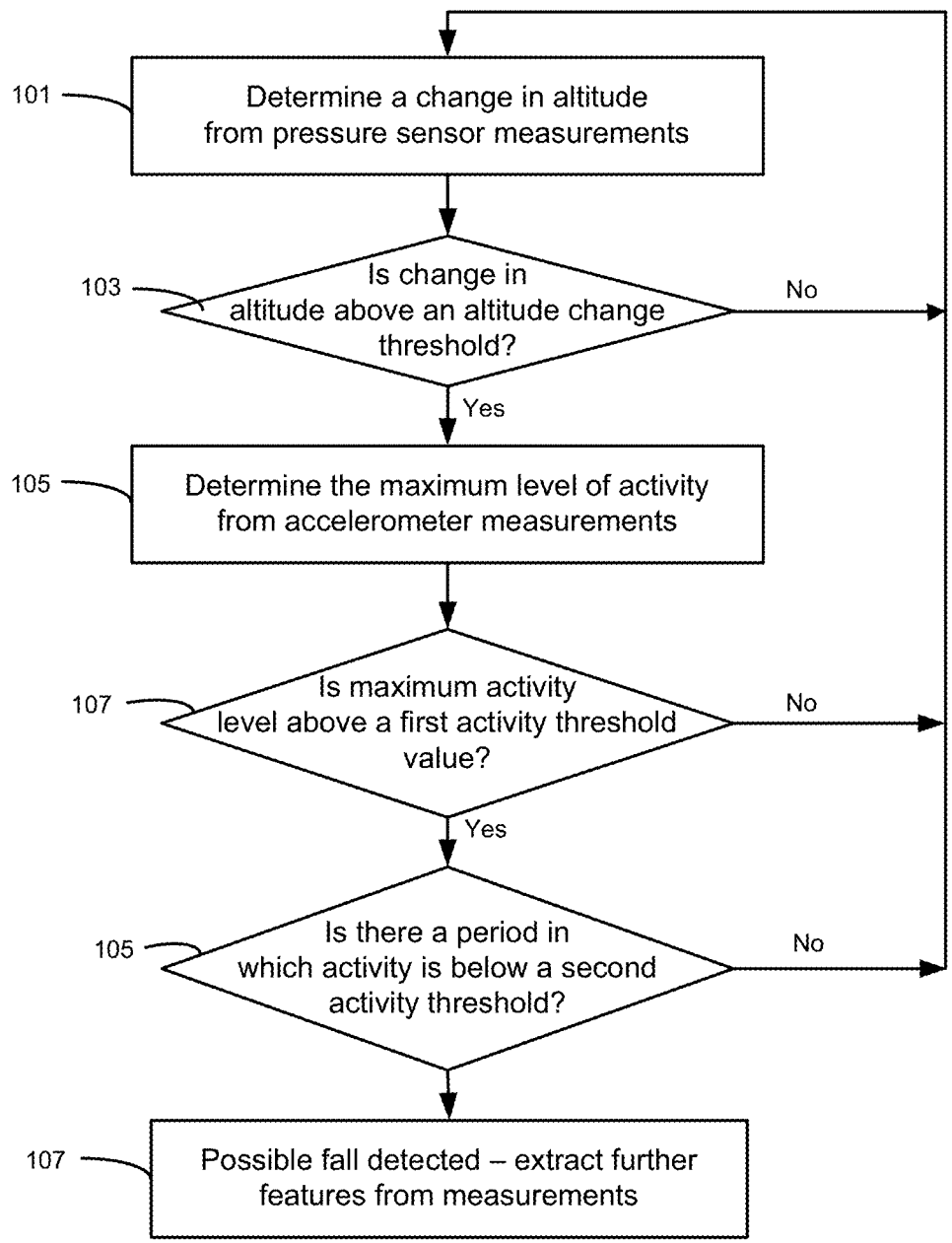
FIG. 2 is a flow chart illustrating the operation of a state machine in managing the extraction and evaluation of features associated with a fall from sensor measurements.
Figure 3A:
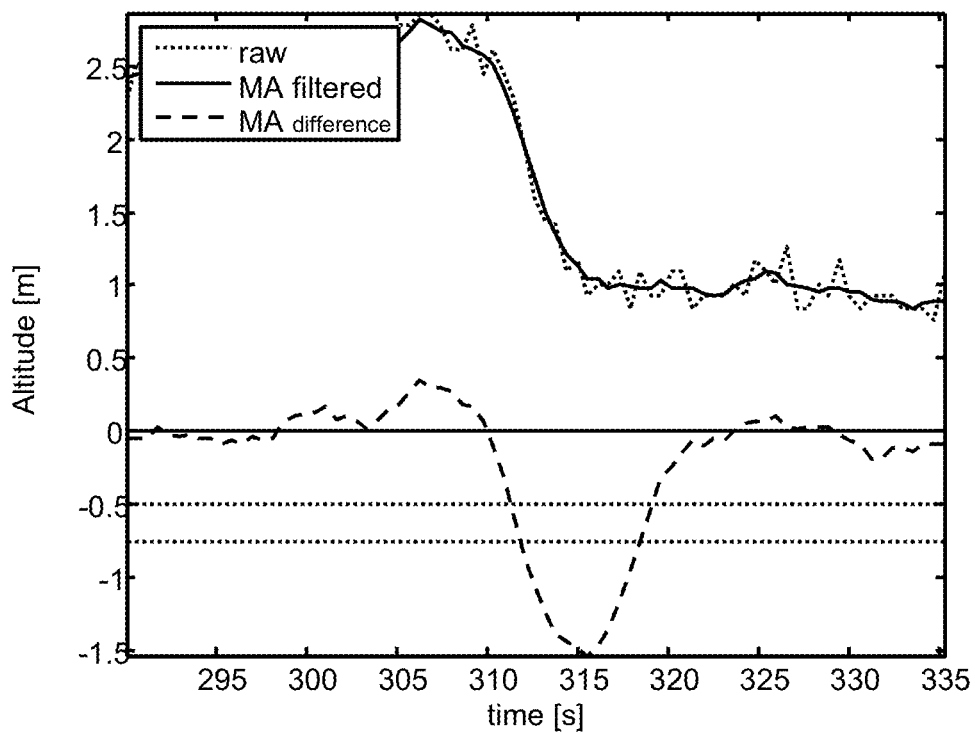
FIG. 3 is a set of graphs illustrating the operation of the method shown in FIG. 2.
Figure 3B:
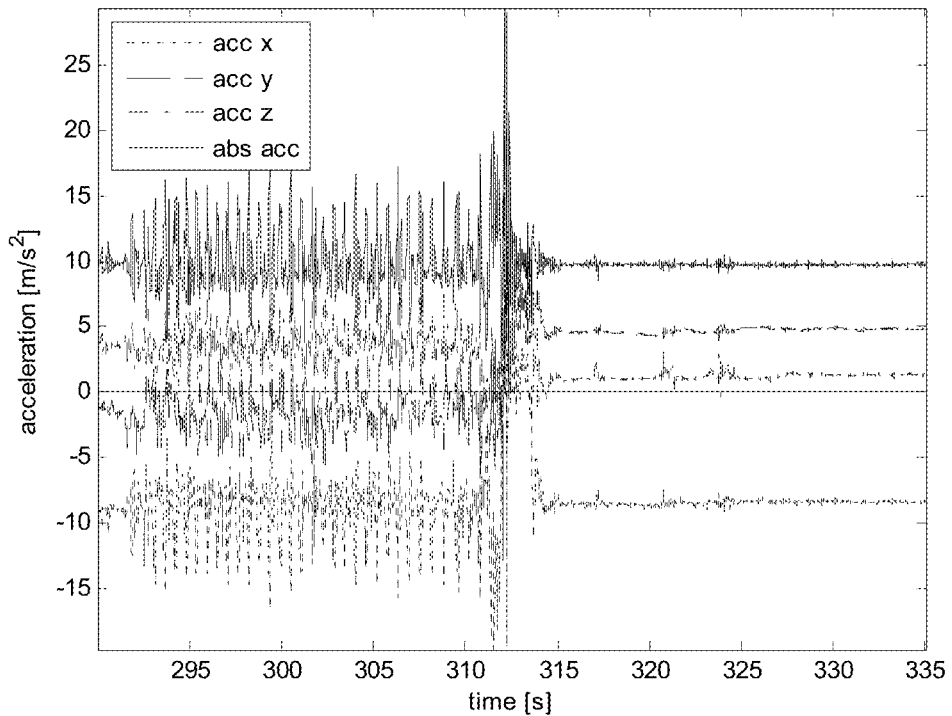
Figure 3C:
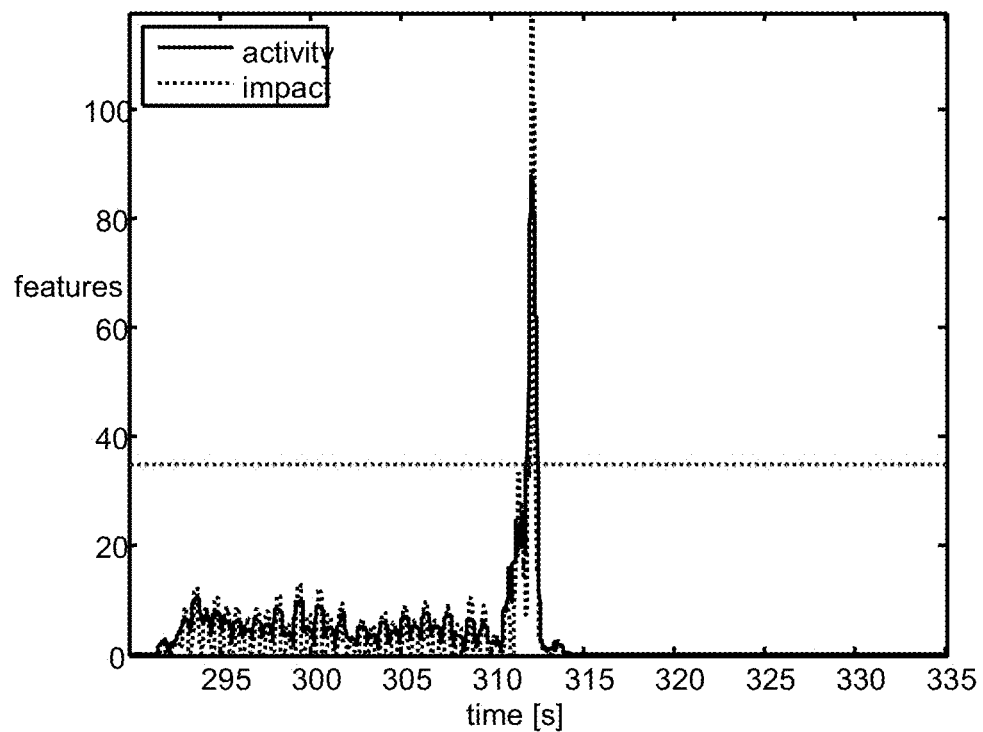
Figure 3D:
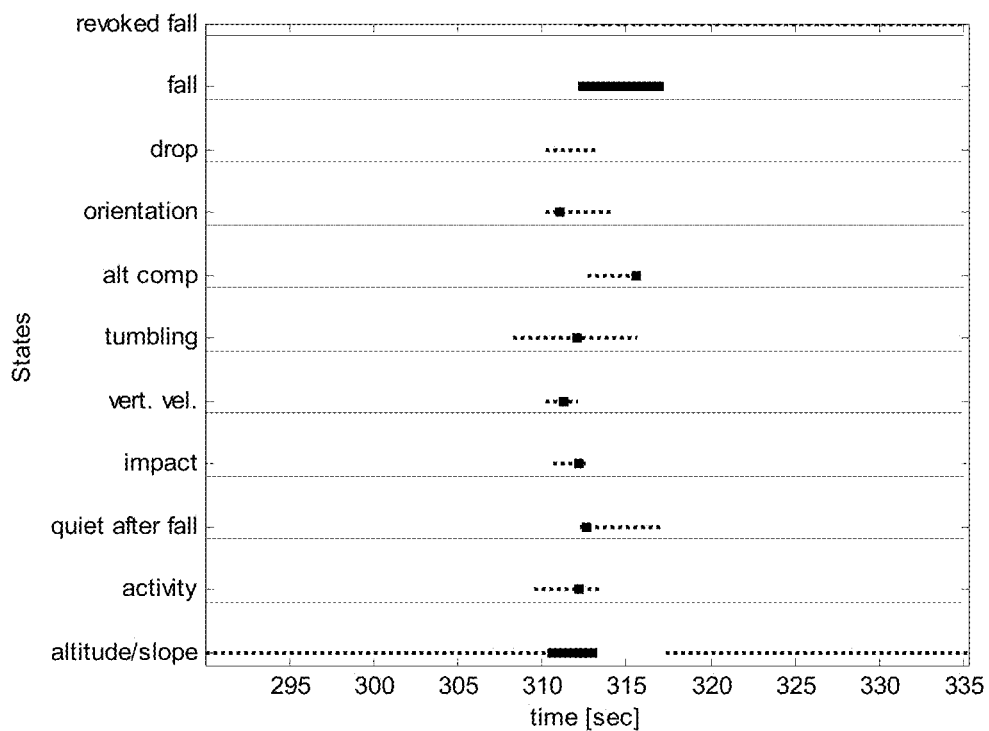

A flow chart illustrating an exemplary state machine operation of the processor 8 is shown in FIG. 2.

Thus, in step 101, the processor extracts a value for a change in altitude from the measurements from the pressure sensor 6. In a specific embodiment, Moving Average (MA) filtering is used to obtain a time series $a_n$ of altitude samples from the air pressure measurements, and an altitude difference signal is computed by taking the difference of the current sample $a_n$ and a previous sample $a_{(n-m)}$ (where m=10 is advantageous) of the MA-filtered altitude samples. In an embodiment, as the sampling rate of the pressure measurement is 1.8 Hz, so the m samples cover a time period of 5.56 seconds.

In step 103, if this difference signal indicates a decrease in altitude of less than 0.5 meters (the value of this altitude change threshold being dependent on the part of the body that the fall detector 2 is to be placed), then the processor 8 decides that no fall has taken place and returns to step 101.

However, if the difference signal indicates a decrease in altitude of more than the altitude change threshold, then it is still possible that a fall has taken place, so the processor 8 continues with the feature extraction and moves to step 105.

In step 105, the processor 8 determines the maximum level of activity during a time window around the time of the altitude decrease from the measurements of the accelerometer 4. The level of activity is a measure of the deviation of the measured accelerations from 1 g, and so represents the user falling, any tumbling occurring during the fall and the presence of an impact. In a specific embodiment, the processor 8 performs the following steps to compute a measure of the level of activity:

a. computing the absolute acceleration by taking the square root of the sum of the squares of each acceleration component, b. subtracting acceleration due to gravity (9.81 ms$^{-2}$) from said absolute acceleration to obtain a normalized absolute acceleration, c. squaring said normalized absolute acceleration to obtain the power of the normalized absolute acceleration, d. taking a moving average (MA) of said power to obtain an MA-filtered power (in a preferred embodiment, the duration of the MA filter is 0.5 seconds), and e. computing the maximum of said MA-filtered power near to or at the time at which the change in altitude exceeded the altitude threshold value (i.e. 0.5 meters).

Then, in step 107, if the maximum level of activity during the time window is less than a first activity threshold value, the processor 8 determines that no fall has taken place and returns to the lowest state, i.e. step 101.

However, if the maximum level of activity is above the first activity threshold value, the processor 8 continues to the next state in which the processor 8 determines if there is a predefined period of time following the maximum level of activity in which the level of activity is relatively low (i.e. a period in which the user of the fall detector 2 might be lying on the ground). In particular, the processor 8 can search for the predefined period of time (for example 1 second) after the time that the maximum level of activity was reached in which the MA-filtered power is below a second activity threshold. The search window can extend for a predefined number of seconds following the time at which the maximum level of activity was reached.

If the processor 8 determines that the level of activity in the search window is below the second activity threshold for at least the predefined period of time, the processor 8 moves to step 111 in which it continues to extract values for other features from the sensor measurements until either a value is extracted that rules out a fall having taken place, or the processor 8 extracts values for all of the required features. However, if the processor 8 does not determine that the level of activity in the search window is below the second activity threshold for at least the predefined period of time, the processor 8 returns to the lowest state, step 101.

The features that can be extracted from the sensor measurements can include measures of any one or more of the following: impact, jerk, vertical velocity, tumbling, compensated drop of altitude, orientation change, activity, the time difference between maximum vertical velocity down from the pressure sensor and the accelerometer respectively, the maximum altitude change and the difference between long and short median-filtered compensated altitude.

The state machine operation of the processor 8 is illustrated in FIGS. 3(*a*)-(*d*). FIG. 3(*a*) is a graph illustrating the altitude measurements from the pressure sensor 6, along with a set of MA-filtered measurements. FIG. 3(*b*) is a graph illustrating the measurements from each axis of the accelerometer 4 along with the absolute value. FIG. 3(*c*) is a graph illustrating the values for activity and impact that have been extracted from the measurements from the accelerometer 4. FIG. 3(*d*) is a graph illustrating when various states of the state machine are activated. In particular, FIG. 3(*d*) shows the time instants at which the processor 8 searches for a particular feature (illustrated by the dotted lines) and the time instants of the actual extraction or recognition of a feature as a single number (shown as a larger dot or a solid line).

FIG. 3(*a*) indicates that the MA-filtered altitude decrease crosses the altitude change threshold (0.5 m) at around time 311 s, which triggers the state machine to extract a value for the activity level.

The dotted line in FIG. 3(*d*) for the "activity" indicates the time window around the time of the altitude decrease in which the maximum activity is computed, and the maximum value for the activity can be seen at time 312 s.

Figure 4:
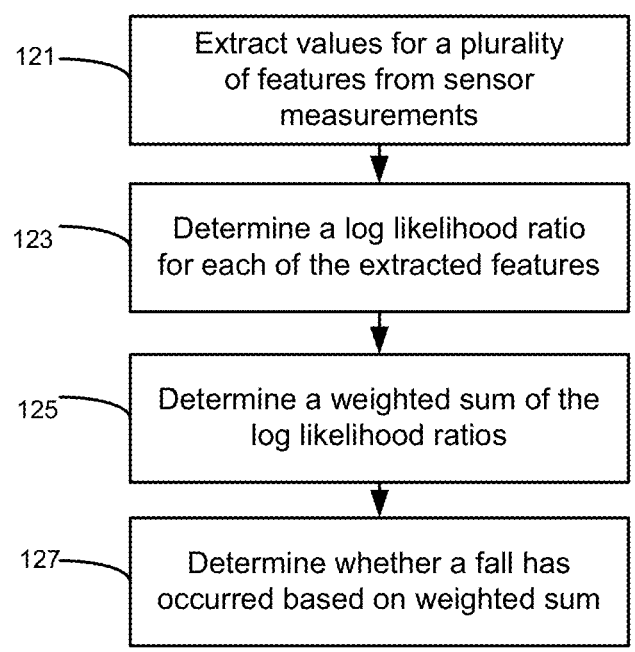
FIG. 4 is a flow chart illustrating the steps in a method according to the invention.

As described above, once values for all of the features have been extracted from the measurements of the accelerometer 4 and pressure sensor 6, the processor 8 must determine whether a fall has taken place. A method of determining whether a fall has occurred is shown in FIG. 4.

In step 121, the processor 8 extracts values for a plurality of features from the sensor measurements as described above with reference to FIG. 2.

In accordance with the invention, a log likelihood ratio for the extracted value of each feature is determined, and the log likelihood ratios are used to decide whether a fall has taken place.

Thus, in step 123, the processor 8 determines a log likelihood ratio for the extracted value of each feature.

From detection theory, it is known that a binary decision (i.e. a fall or non-fall) can be based on a likelihood ratio Λ, given by:

$$\Lambda(\text{features}) = \frac{Pr(\text{features} \mid \text{fall})}{Pr(\text{features} \mid \text{nonfall})}, \quad \begin{array}{l} \text{fall if } \Lambda > \Lambda_{threshold} \\ \text{nonfall if } \Lambda < \Lambda_{threshold} \end{array} \quad (1)$$

The threshold, $\Lambda_{threshold}$, depends on the prior probabilities and costs of decisions for a fall and non-fall, respectively. If prior probabilities are unknown, the Neyman-Pearson criterion can be used, where the false alarm rate is set to fix the costs, and subsequently the detection probability can be maximised for a given false alarm rate. Similarly, it can be shown that a decision can be based on a Log Likelihood Ratio (LLR) which is given by:

$$LLR(\text{features}) = \log(\Lambda(\text{features})), \quad \begin{array}{l} \text{fall if } LLR > LLR_{threshold} \\ \text{nonfall if } LLR < LLR_{threshold} \end{array} \quad (2)$$

If features are statistically independent, it can be shown that the LLR of a set of features equals the sum of the LLRs of the individual features:

$$LLR(\text{features}) = \sum_i LLR(\text{feature}_i) \quad (3)$$

Figure 5:
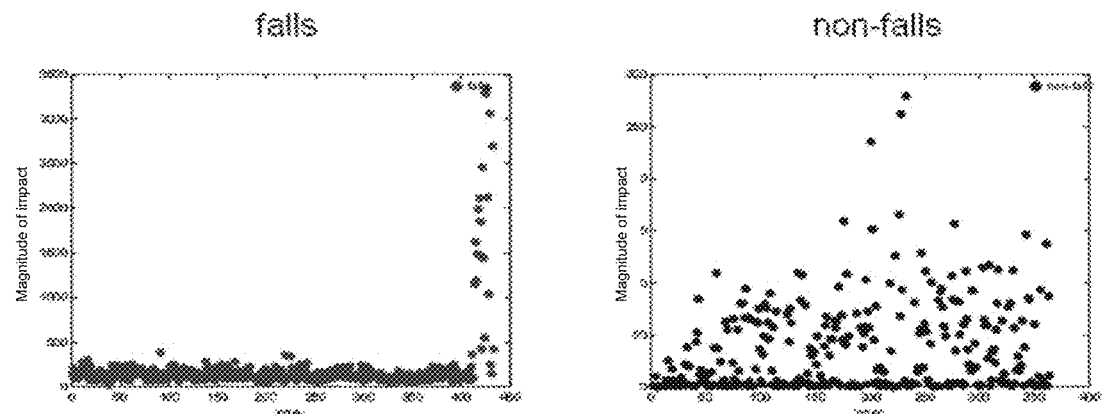
FIG. 5 shows two graphs illustrating the measured impact magnitude for a series of falls and non-falls.

For example, consider the calculation of the Log Likelihood Ratio LLR for the feature "impact". FIG. 5 illustrates the magnitude of the impact measured in a few hundred events for falls and non-falls respectively (the non-fall events being events classified as non-falls that satisfy the thresholds used by the state machine in FIG. 2 and that result in the state machine computing the LLRs in accordance with step 123).

Figure 6:
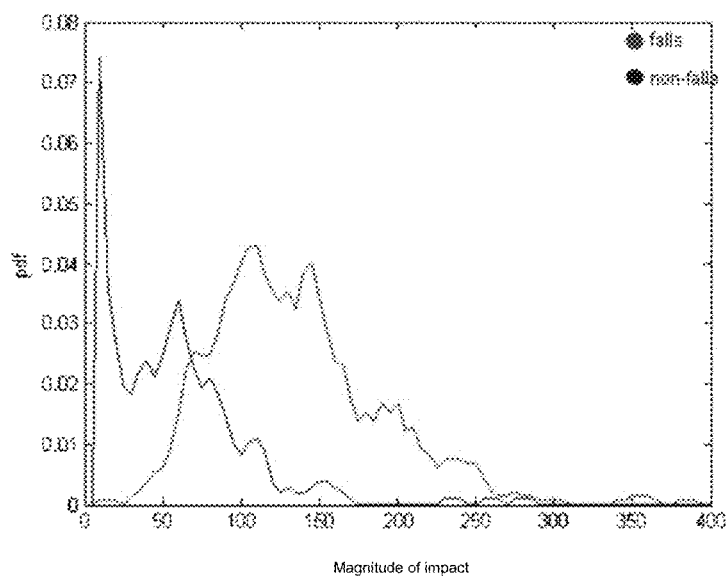
FIG. 6 is a graph illustrating probability density functions for the impact magnitudes shown in FIG. 4.

From this, a probability density function can be calculated for the magnitude of the impact for a fall or non-fall respectively. These probability density functions are shown in FIG. 6.

From these probability density functions, it is possible to determine the log likelihood ratio of the impact magnitude using equations (1) and (2) above to give:

$$LLR(\text{impact}) = \log(\Lambda(\text{impact})) \quad (4)$$
$$= \log\left[\frac{Pr(\text{impact} \mid \text{fall})}{Pr(\text{impact} \mid \text{nonfall})}\right]$$

Figure 7:
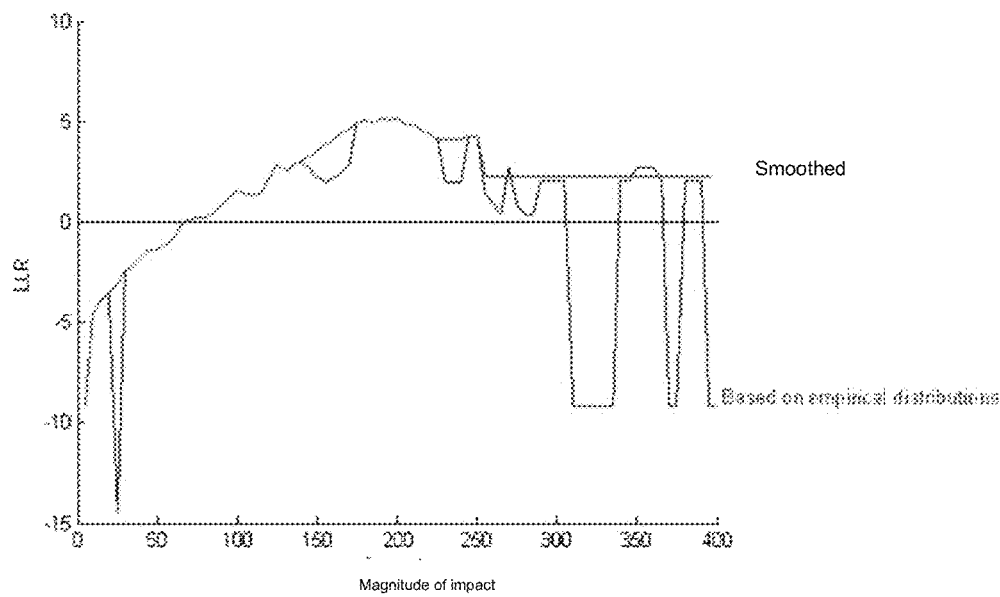
FIG. 7 is a graph illustrating the log likelihood ratio for the impact feature as a function of impact magnitude.

A graph illustrating the determined log likelihood ratios for impact magnitude is shown in FIG. 7. It can be seen that there is a large variation in the log likelihood ratios due to measurement noise (i.e. insufficient observations), so it is necessary to generate a smoothed line.

The processor 8 determines the log likelihood ratio for impact magnitude using a look-up table stored in the fall detector 2 whose values are based on the smoothed curve in FIG. 7. Thus, on determining the magnitude of an impact in step 121 of the method in FIG. 4, the processor 8 can use the look-up table to determine the associated value of the log likelihood ratio in step 123. Generally, an impact having a positive value for the log likelihood ratio increases the probability that the processor 8 will determine that a fall has taken place, while a negative log likelihood ratio will reduce the probability that the processor 8 decides that a fall has taken place.

It will be appreciated that the fall detector 2 will include respective look-up tables for each of the features that can be extracted from the measurements of the accelerometer 4 and pressure sensor 6, with the values in each of these look-up tables being derived from graphs analogous to that shown in FIG. 7 for impact magnitude.

As described above, this log likelihood ratio, along with log likelihood ratios for other extracted features determined in step 123, is used by the processor 8 to determine if a fall has taken place.

As described above and shown in equation (3), when features are statistically independent, the log likelihood ratio of a set of features equals the sum of the log likelihood ratios of the individual features.

However, as the various features extracted by the processor 8 from the sensor measurements are not independent, equation (3) cannot be used to produce a reliable result. Therefore, in a preferred embodiment of the invention, the processor 8 determines a weighted sum of the log likelihood ratios to produce an overall log likelihood ratio for the event (step 125). Thus, the processor 8 determines the result of equation (5) below:

$$LLR(\text{features}) = \sum_i w_i \cdot LLR(\text{feature}_i) \quad (5)$$

Some exemplary values for the weighting values $w_i$ for the features listed above are given in the table below:

| Feature | Weighting value, $w_i$ |
| --- | --- |
| Compensated drop in altitude | 0.9952 |
| Activity | 0.2798 |
| Impact | 0.2771 |
| Jerk | 0.2976 |
| Tumbling | 0.1703 |
| Vertical velocity | 0.3660 |
| Orientation change | 0.3467 |
| Time difference between maximum velocity from pressure sensor and accelerometer measurements | 0.6656 |
| Maximum altitude deviation | 0.8121 |
| Difference between long and short median-filtered compensated altitude | 0.8382 |

However, where look-up tables for the log likelihood ratios of each feature are stored in the fall detector 2, the effect of the weighting value $w_i$ on the log likelihood ratios can be taken into account when compiling the look-up tables (i.e. the values in the look-up table can be equal to the log likelihood ratio multiplied by the appropriate weighting value). In this way, the processor 8 can simply look-up the weighted log likelihood ratio for each of the features in step 123 and add these together in step 125 to produce the overall log likelihood ratio.

The processor 8 then uses this weighted sum $LLR_{sum}$ to determine if a fall has taken place (step 127). In particular, the processor 8 compares the weighted sum $LLR_{sum}$ to a detection threshold value (e.g. 10), and if the weighted sum exceeds the detection threshold value it is decided that a fall has taken place. If the weighted sum is below the detection threshold value, then it is decided that a fall has not taken place. The selection of the detection threshold value determines the point on the ROC that the fall detector 2 operates.

Figure 8:
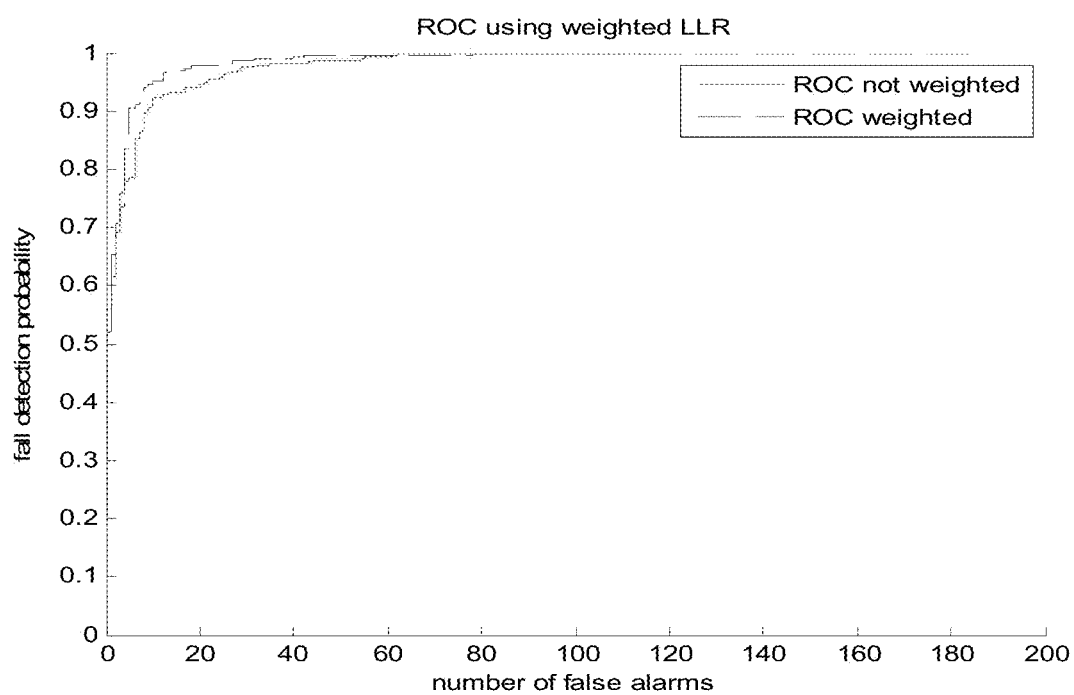
FIG. 8 is a graph illustrating the Receiver Operating Curves for a weighted and unweighted sum of the log likelihood ratios.
Figure 9:
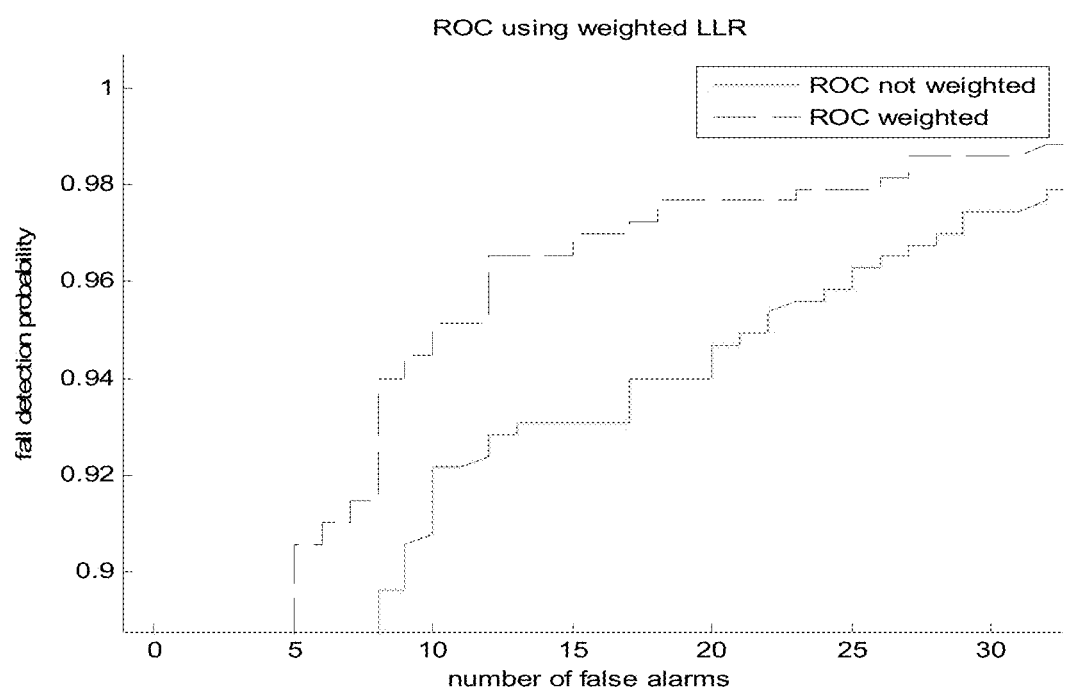
FIG. 9 is a graph showing a portion of the Receiver Operating Curves of FIG. 8 in more detail.

The value of the weights $w_i$ can also be chosen to optimize the Receiver Operating Characteristic (ROC). For example, FIG. 8 illustrates two different ROC curves, both based on the processor 8 extracting a set of ten features from a set of sensor measurements, with one curve corresponding to a log likelihood ratio sum using uniform weighting (i.e. 1) for all features (represented by the solid line) and the other curve corresponding to a log likelihood ratio sum using a near-optimal weight distribution (represented by the dashed line). FIG. 9 shows a portion of the graph in FIG. 8 in more detail. The x-axis of the graphs in FIGS. 8 and 9 represents the total number of false alarms over a period of approximately thirty months. Therefore, having a fall detection probability of say, 96%, leads to around 12 false alarms over a period of thirty months (i.e. less than 0.5 false alarms per user per month). Thus, it can be seen that the weighted sum of the log likelihood ratios more than halves the false alarm rate with a detection probability of around 95%.

There is therefore provided an improved method for detecting falls that determines log likelihood ratios for features extracted from sensor measurements.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of detecting a fall by a user, the method comprising:
with a processor or computer, processing measurements obtained from one or more sensors to extract a respective value for a plurality of features associated with a fall, wherein processing the measurements includes processing measurements obtained from an air pressure sensor to extract values indicating changes in altitude;
with a processor or computer, determining a respective log likelihood ratio for each of said extracted values;
with a processor or computer, determining whether the user has fallen based on the determined log likelihood ratios; and
with a transmitter, in response to determining that the user has fallen, transmitting a signal indicating the user has fallen.

2. The method as claimed in claim 1, wherein the step of determining whether the user has fallen comprises determining whether the user has fallen based on a sum of the log like ratios for each of said extracted values.

3. The method as claimed in claim 2, wherein the step of determining whether the user has fallen comprises determining whether the user has fallen based on a weighted sum of the log likelihood ratios for each of said extracted values.

4. The method as claimed in claim 2, wherein the step of determining whether the miser has fallen comprises comparing the sum of the determined log likelihood ratios to a detection threshold.

5. The method as claimed in claim 4, wherein the step of determining whether the user has fallen comprises determining that the user has fallen in the event that the sum of the determined log likelihood ratios is greater than the threshold, and that the user has not fallen in the event that the sum of the determined log likelihood ratios is less than the threshold.

6. The method as claimed in claim 1, wherein the step of determining the log likelihood ratio comprises using said extracted value to look up the log likelihood ratio in a table.

7. The method as claimed in claim 6, wherein the table comprises log likelihood ratios to which the appropriate weighting has been applied.

8. The method as claimed in claim 1, wherein, in the event that a change in altitude exceeds an altitude change threshold, the step of processing measurements further comprises:

processing measurements obtained from an accelerometer to determine a maximum level of activity during a time window around the time that the change in altitude exceeded the altitude change threshold.

9. The method as claimed in claim 8, wherein, in the event that the maximum level of activity during the time window exceeds a first activity threshold, the step of processing measurements further comprises:
processing the measurements obtained from the accelerometer to determine whether there is a predefined period of time within a search window following the maximum level of activity during which the level of activity is below a second activity threshold.

10. The method as claimed in claim 9, wherein, in the event that there is a predefined period of time within a search window following the maximum level of activity during which the level of activity is below the second activity threshold, the step of processing measurements further comprises:
extracting values for further features associated with a fall; and wherein the steps of determining a log likelihood ratio and determining whether the user has fallen are only executed if the extracted values for all of the further features do not preclude a fail having taken place.

11. A non-transitory computer program product carrying computer-readable code that, when executed on a suitable computer or processor, is configured to cause the computer or processor to perform the steps in the method defined in claim 1.

12. A fall detector, comprising:
a means for determining altitude changes;
an accelerometer configured to determine activity levels;
a processor that is configured to:
extract altitude change values from the determined altitude changes,
determine an altitude change log likelihood ratio for said altitude change values,
when the altitude change log ratio exceeds an altitude change threshold, extract activity level values from the determined activity levels,
determine an activity level log ratio for the activity level values; and
determine whether the user has fallen based on the determined altitude change and activity level log likelihood ratios.

13. An apparatus for detecting a fall by a user, the apparatus comprising:
an altitude sensor means for determining a change in altitude and outputting an altitude signal, the altitude sensor means being configured to be attached to the user;
a computer or processor programmed to:
receive the altitude signal,
extract altitude values from the altitude signal,
determine log likelihood ratios for the altitude values,
analyze the log likelihood ratios to determine whether the user has fallen; and
a transmitter configured to transmit a fall signal when the user is determined to have fallen.

14. The apparatus as claimed in claim 13, further including:
an activity sensor means for determining an activity level and outputting an activity signal, the activity sensor means being configured to be attached to the user; and
wherein the processor is further programmed to:
receive the activity signal,
extract activity values from the activity signal, and
determine actively log likelihood ratios for the activity values to be analyzed with the altitude log likelihood ratios to determine whether the user has fallen.

15. The apparatus as claimed in claim 14, wherein the activity values are extracted in response to is change in extracted altitude values exceeding an altitude change threshold.

16. The apparatus as claimed in claim 15, further including:
other feature sensor means for determining other features and outputting other feature signals; and
wherein the processor is further configured to extract other feature values and determine that the user has fallen only if the extracted other feature values do not preclude a fall having taken place.

17. The apparatus as claimed in claim 14, wherein the activity sensor means includes an accelerometer.

18. The apparatus as claimed in claim 13, wherein the altitude sensor means includes an air pressure sensor.

* * * * *